(12) United States Patent
Welch et al.

(10) Patent No.: US 7,404,411 B2
(45) Date of Patent: Jul. 29, 2008

(54) METHOD AND APPARATUS FOR ANALYSIS OF RELATIVE LEVELS OF BIODIESEL IN FUELS BY NEAR-INFRARED SPECTROSCOPY

(75) Inventors: William T. Welch, Ashland, KY (US); Roy R. Bledsoe, Jr., Huntington, WV (US); Brian K. Wilt, Flatwoods, KY (US)

(73) Assignee: Marathon Ashland Petroleum LLC, Findlay, OH (US)

( * ) Notice: Subject to any disclaimer, the term of this patent is extended or adjusted under 35 U.S.C. 154(b) by 484 days.

(21) Appl. No.: 11/088,429

(22) Filed: Mar. 23, 2005

(65) Prior Publication Data

US 2006/0213554 A1 Sep. 28, 2006

(51) Int. Cl.
G05D 11/13 (2006.01)
(52) U.S. Cl. ............................................. 137/3; 137/93
(58) Field of Classification Search ...................... 137/3, 137/93; 250/339.09, 339.12, 343
See application file for complete search history.

(56) References Cited

U.S. PATENT DOCUMENTS

| | | |
|---|---|---|
| 4,798,463 A | 1/1989 | Koshi |
| 4,963,745 A | 10/1990 | Maggard |
| 5,145,785 A | 9/1992 | Maggard et al. |
| 5,223,714 A | 6/1993 | Maggard |
| 5,243,546 A | 9/1993 | Maggard |
| 5,348,645 A | 9/1994 | Maggard et al. |
| 5,349,188 A | 9/1994 | Maggard |
| 5,349,189 A | 9/1994 | Maggard |
| 5,362,965 A | 11/1994 | Maggard |
| 5,370,790 A | 12/1994 | Maggard et al. |
| 5,381,002 A | 1/1995 | Morrow et al. |
| 5,416,323 A | 5/1995 | Hoots et al. |
| 5,452,232 A | 9/1995 | Espinosa et al. |
| 5,596,196 A | 1/1997 | Cooper et al. |
| 5,684,580 A | 11/1997 | Cooper et al. |
| 5,712,481 A | 1/1998 | Welch et al. |
| 5,856,869 A | 1/1999 | Cooper et al. |
| 5,892,228 A | 4/1999 | Cooper et al. |
| 5,916,433 A | 6/1999 | Tejada et al. |
| 6,015,440 A | 1/2000 | Noureddini |
| 6,070,128 A | 5/2000 | Descales et al. |

(Continued)

OTHER PUBLICATIONS

ARS Article—NIR helps Turn Vegatable Oil inot High-Quality Biofuel. Jun. 15, 1999, Agriculture research Service.*

*Primary Examiner*—Ramesh Krishnamurthy
(74) *Attorney, Agent, or Firm*—Emch, Schaffer, Schaub & Porcello Co., L.P.A.

(57) ABSTRACT

A process and system for the analysis and/or control of a mixture of liquid hydrocarbons and biodiesel to determine biodiesel concentration includes a) measuring the near infrared absorption in at least two of the bands of two absorption bands from a portion of the range of 800-2500 nm; in particular 1100-2500 nm which are used to quantify the biodiesel content. b) taking each of the absorbances measured, or a mathematical function thereof, c) performing at least one mathematical computing or statistical treatment using the above absorbances or functions as individual independent variables, d) assigning and applying weighting constants or their equivalents to the independent variables, and, optionally e) applying the above steps using known compositions to calibrate the instrument and determine the weighting constants or equivalents, and further optionally f) outputting a signal indicative of the biodiesel concentration in the mixture, based on the absorbances or functions.

23 Claims, 5 Drawing Sheets

| Diesel | Bio-diesel Source | Volume % Biodiesel | FOSS NIRSystem | Vendor A[2] | Vendor B[2] |
|---|---|---|---|---|---|
| Pipeline | Terminal | 2.00 | 2.09 | 1.6 | 1.7 |
| Refinery C | Yellow Grease GI | 2.00 | 2.06 | 1.7 | 1.8 |
| Refinery C | Soy GI | 2.00 | 2.00 | 1.6 | 1.8 |
| Tank | ASTM D-903 BIO | 2.00 | 2.05 | 1.8 | 1.8 |
| Refinery C | ASTM D-903 BIO | 2.00 | 2.00 | 1.7 | 1.8 |
| Tank | Yellow Grease GI | 2.00 | 1.93[1] | 1.9 | 1.9 |
| Tank | Soy GI | 2.00 | 1.92 | 1.9 | 1.9 |
| Refinery C | Animal Fat GI | 2.00 | 1.97 | 1.6 | 1.8 |
| | Average | 2.00 | 2.01 | 1.73 | 1.81 |
| | Standard Deviation | 0.00 | 0.06 | 0.13 | 0.06 |

[1]Sample was included in the NIR calibration set.
[2]Submitted to vendors as blind samples.

U.S. PATENT DOCUMENTS

| | | |
|---|---|---|
| 6,087,662 A | 7/2000 | Wilt et al. |
| 6,140,647 A | 10/2000 | Welch et al. |
| 6,174,501 B1 | 1/2001 | Noureddini |
| 6,203,585 B1 | 3/2001 | Majerczak |
| 6,235,104 B1 | 5/2001 | Chattopadhyay |
| 6,348,074 B2 | 2/2002 | Wenzel |
| 6,395,228 B1 | 5/2002 | Maggard et al. |
| 6,740,226 B2 | 5/2004 | Mehra et al. |
| 2006/0037237 A1* | 2/2006 | Copeland et al. .............. 44/605 |

* cited by examiner

Fig. 1 - Table 1

| Diesel | Bio-diesel Source | Volume % Biodiesel | FOSS NIRSystem | Vendor A[2] | Vendor B[2] |
|---|---|---|---|---|---|
| Pipeline | Terminal | 2.00 | 2.09 | 1.6 | 1.7 |
| Refinery C | Yellow Grease GI | 2.00 | 2.06 | 1.7 | 1.8 |
| Refinery C | Soy GI | 2.00 | 2.00 | 1.6 | 1.8 |
| Tank | ASTM D-903 BIO | 2.00 | 2.05 | 1.8 | 1.8 |
| Refinery C | ASTM D-903 BIO | 2.00 | 2.00 | 1.7 | 1.8 |
| Tank | Yellow Grease GI | 2.00 | 1.93[1] | 1.9 | 1.9 |
| Tank | Soy GI | 2.00 | 1.92 | 1.9 | 1.9 |
| Refinery C | Animal Fat GI | 2.00 | 1.97 | 1.6 | 1.8 |
| | Average | 2.00 | 2.01 | 1.73 | 1.81 |
| | Standard Deviation | 0.00 | 0.06 | 0.13 | 0.06 |

[1]Sample was included in the NIR calibration set.
[2]Submitted to vendors as blind samples.

Fig. 2 - Table 2

| Diesel source | Biodiesel Source | Volume % Bio-diesel | FOSS NIRSystems | Vendor A[4] | Vendor B[4] |
|---|---|---|---|---|---|
| Pipeline | None | 0.00 | 0.1 | 0.00 | 0.0 |
| Pipeline | Terminal | 0.50 | 0.65 | 0.3 | 0.3 |
| Pipeline | Terminal | 1.00 | 1.09 | 0.7 | 0.8 |
| Pipeline | Terminal | 1.50 | 1.67 | 1.2 | 1.2 |
| Pipeline | Terminal | 2.00 | 2.09 | 1.6 | 1.7 |
| Refinery C | Yellow Grease GI | 2.00 | 2.06 | 1.7 | 1.8 |
| Refinery C | Soy GI | 2.00 | 2.00 | 1.6 | 1.8 |
| Tank | ASTM D-903 BIO | 2.00 | 2.05 | 1.8 | 1.8 |
| Refinery C | ASTM D-903 BIO | 2.00 | 2.00 | 1.7 | 1.8 |
| Tank | Yellow Grease GI | 2.00 | 1.93[3] | 1.9 | 1.9 |
| Tank | Soy GI | 2.00 | 1.92 | 1.9 | 1.9 |
| Refinery C | Animal GI | 2.00 | 1.97 | 1.6 | 1.8 |
| Tank | ASTM D-903 BIO | 5.00 | 5.04 | 4.7 | 5.2 |
| Pipeline | Yellow Grease GI | 10.00 | 9.88 | 9.7 | 8.9 |
| Refinery C | Soy GI | 15.00 | 15.02 | 14.6 | 15.0 |
| ASTM Round Robin | Exxon D-903 | 20.00 | 20.13 | 20.1 | 20.5 |
| ASTM Round Robin | MS Chem Lab D-904 | 20.00 | 20.00 | 20.2 | 18.9 |
| Tank | Animal GI | 25.00 | 25.21 | 25.0 | 23.2 |
| Refinery C | None | 0.00 | 0.0 | 0.0 | 0.0 |
| Tank | None | 0.00 | 0.0 | 0.0 | 0.0 |
| SEP[5] | | | 0.10 | 0.27 | 0.64 |

[3]Sample was included in the NIR calibration set; [4]Submitted to vendors as blind samples; [5]Standard Error of Prediction

Fig. 3 - Table 3

| Diesel Source | 0.5 | 1.0 | 2.0 | 3.0 | 5.0 | 10.0 | 15.0 | 20.0 | 25.0 |
|---|---|---|---|---|---|---|---|---|---|
| Refinery A | Indy | AF | 903 B | Indy | Soy | AF | YG | Indy | Soy |
| Refinery B | AF | 903B | AF | Soy | Indy | Indy | 903B | AF | YG |
| Refinery C | 903B | Soy | YG | 903B | AF | YG | Indy | Soy | AF |
| Refinery D | YG | Indy | Soy | YG | 903B | Soy | AF | YG | 903B |
| Refinery E | Soy | YG | Indy | AF | YG | 903B | Soy | 903B | Indy |
| Refinery F | Indy | AF | 903 B | Indy | Soy | AF | YG | NA | NA |
| Refinery G | Soy | YG | Indy | AF | YG | 903B | Soy | Indy | 903B |

Indy - a sample of soy derived biodiesel from the Indianapolis Terminal SB-D
903B - ASTM cetane round robin, biodiesel D-903 BIO
Soy - soy derived, from vendor GI
YG - yellow grease derived, from vendor G
AF - animal derived, from vendor G

Fig. 4A - Table 4

| Diesel Source | Biodiesel | % Vol Added Biodiesel | NIR Calculated | Residue Biodiesel |
|---|---|---|---|---|
| Refinery E | Yellow Grease | 2.00 | 1.93 | -0.07 |
| Refinery E | Soy | 0.50 | 0.58 | 0.08 |
| Refinery E | Yellow Grease | 1.00 | 1.04 | 0.04 |
| Refinery E | Terminal | 2.00 | 1.93 | -0.07 |
| Refinery E | Animal Fat | 3.00 | 3.01 | 0.01 |
| Refinery E | Yellow Grease | 5.00 | 4.96 | -0.04 |
| Refinery E | ASTM 903 BIO | 10.00 | 10.08 | 0.08 |
| Refinery E | Soy | 15.00 | 15.14 | 0.14 |
| Refinery E | ASTM 903 BIO | 20.00 | 19.98 | -0.02 |
| Refinery E | Terminal | 25.00 | 24.86 | -0.14 |
| Refinery D | None | 0.00 | -0.01 | -0.01 |
| Refinery D | Yellow Grease | 0.50 | 0.53 | 0.03 |
| Refinery D | Soy | 2.00 | 1.99 | -0.01 |
| Refinery D | Yellow Grease | 3.00 | 2.97 | -0.03 |
| Refinery D | ASTM 903 BIO | 5.00 | 4.99 | -0.01 |
| Refinery D | Soy | 10.00 | 10.07 | 0.07 |
| Refinery D | Animal Fat | 15.00 | 15.03 | 0.03 |
| Refinery D | Yellow Grease | 20.00 | 19.99 | -0.01 |
| Refinery D | ASTM 903 BIO | 25.00 | 24.98 | -0.02 |
| Refinery B | None | 0.00 | 0.08 | 0.08 |
| Refinery B | Animal Fat | 0.50 | 0.58 | 0.08 |
| Refinery B | ASTM 903 BIO | 1.00 | 1.03 | 0.03 |
| Refinery B | Animal Fat | 2.00 | 2.00 | 0.00 |
| Refinery B | Soy | 3.00 | 3.00 | 0.00 |
| Refinery B | Terminal | 10.00 | 10.01 | 0.01 |
| Refinery B | ASTM 903 BIO | 15.00 | 14.98 | -0.02 |
| Refinery B | Animal Fat | 20.00 | 19.86 | -0.14 |
| Refinery B | Yellow Grease | 25.00 | 24.91 | -0.09 |
| Refinery A | None | 0.00 | -0.05 | -0.05 |
| Refinery A | Terminal | 0.50 | 0.44 | -0.06 |
| Refinery A | Animal Fat | 1.00 | 1.00 | 0.00 |
| Refinery A | ASTM 903 BIO | 2.00 | 1.98 | -0.02 |
| Refinery A | Terminal | 3.00 | 2.93 | -0.07 |
| Refinery A | Soy | 5.00 | 4.99 | -0.01 |
| Refinery A | Animal Fat | 10.00 | 10.06 | 0.06 |
| Refinery A | Yellow Grease | 15.00 | 15.05 | 0.05 |
| Refinery A | Terminal | 20.00 | 19.95 | -0.05 |
| Refinery A | Soy | 25.00 | 25.13 | 0.13 |
| Refinery C | None | 0.00 | 0.03 | 0.03 |
| Refinery C | ASTM 903 BIO | 0.50 | 0.43 | -0.07 |
| Refinery C | Soy | 1.00 | 0.93 | -0.07 |
| Refinery C | Yellow Grease | 2.00 | 1.94 | -0.06 |

Fig. 4B – Table 4 continued

| Diesel Source | Biodiesel | % Vol Added Biodiesel | NIR Calculated | Residue Biodiesel |
|---|---|---|---|---|
| Refinery C | Soy | 3.00 | 2.96 | -0.04 |
| Refinery C | Animal Fat | 5.00 | 4.88 | -0.12 |
| Refinery C | Yellow Grease | 10.00 | 10.13 | 0.13 |
| Refinery C | Terminal | 15.00 | 15.15 | 0.15 |
| Refinery C | Soy | 20.00 | 19.94 | -0.06 |
| Refinery C | Animal Fat | 25.00 | 24.98 | -0.02 |
| Refinery F | None | 0.00 | -0.09 | -0.09 |
| Refinery F | Terminal | 0.50 | 0.53 | 0.03 |
| Refinery F | Animal Fat | 1.00 | 1.05 | 0.05 |
| Refinery F | ASTM 903 BIO | 2.00 | 1.97 | -0.03 |
| Refinery F | Terminal | 3.00 | 3.00 | 0.00 |
| Refinery F | Soy | 5.00 | 5.02 | 0.02 |
| Refinery F | Animal Fat | 10.00 | 9.93 | -0.07 |
| Refinery F | Yellow Grease | 15.00 | 15.01 | 0.01 |
| Refinery G | None | 0.00 | -0.02 | -0.02 |
| Refinery G | Soy | 0.50 | 0.48 | -0.02 |
| Refinery G | Yellow Grease | 1.00 | 1.08 | 0.08 |
| Refinery G | Terminal | 2.00 | 1.98 | -0.02 |
| Refinery G | Animal Fat | 3.00 | 2.95 | -0.05 |
| Refinery G | Yellow Grease | 5.00 | 5.05 | 0.05 |
| Refinery G | ASTM 903 BIO | 10.00 | 10.07 | 0.07 |
| Refinery G | Soy | 15.00 | 15.10 | 0.10 |
| Refinery G | Terminal | 20.00 | 20.00 | 0.00 |
| Refinery G | ASTM 903 BIO | 25.00 | 25.00 | 0.00 |

Fig. 7 - Tables 5A and 5B

| Table 5A. Calculated from five consecutive back-to-back spectra (Average of 32 scans per spectra) | | Table 5B. Calculated from five consecutive spectra withdrawing and cleaning the probe between scans. (Average of 32 scans per spectra) | |
|---|---|---|---|
| Run Number | Biodiesel | Run Number | Biodiesel |
| 1 | 2.01 | 1 | 1.96 |
| 2 | 2.03 | 2 | 1.88 |
| 3 | 1.99 | 3 | 1.85 |
| 4 | 2.00 | 4 | 1.83 |
| 5 | 1.96 | 5 | 1.85 |
| Average | 2.00 | Average | 1.87 |
| Std Dev | 0.03 | Std Dev | 0.05 |

Calibration Set : Calculated vs Lab Data

Validation Set : Calculated vs Lab Data

METHOD AND APPARATUS FOR ANALYSIS OF RELATIVE LEVELS OF BIODIESEL IN FUELS BY NEAR-INFRARED SPECTROSCOPY

BACKGROUND OF THE INVENTION

The invention describes the use of Near IR spectroscopy to determine the amount of biodiesel in a conventional diesel by collecting the NIR spectrum, applying a mathematical function to the absorbance spectrum, and using a multivariate regression model to predict the biodiesel content. It is shown that multiple sources of biodiesel, and multiple sources of conventional diesel can be used in a single regression model. The predicted result can be used to control an automated or manual blending process at a petroleum refinery, product terminal, or truck loading facility.

Biodiesel is an alternative fuel source derived from soy, animal fat, vegetable oil, or restaurant oil waste. It is produced in a transesterifiction reaction using the oil or fat and an alcohol such as methanol to produce a methyl ester. In the near future, it is expected some states are going to mandate the addition of biodiesel to conventional diesel refined from petroleum crude oil. Simple, rapid analytical techniques will be needed to measure the amount of biodiesel added to a conventional fuel in the blending process. Spectroscopy, more specifically Near Infrared (NIR) spectroscopy, is well suited to make this determination.

Near IR has been used effectively to quantitatively monitor the physical properties of hydrocarbon fuels. Several patents are cited. The technique is non-destructive to the sample, multiple properties can be predicted from a single spectrum, and it has been shown it can be placed on-line to monitor a process or blender stream in real-time.

In literature cited, Knothe describes the use of Near IR to quantitatively monitor the transesterification biodiesel reaction. Using regions in the NIR near 6005 cm$^{-1}$ and 4425-4430 cm$^{-1}$ it is possible to quantify the amount of vegetable oil residual in the biodiesel as the reaction progresses. Previously, gas chromatography (GC) had been used to monitor the reaction, but NIR is faster and the use of in-line sample probes makes it more convenient.

Knothe also describes a method in the literature to predict biodiesel content in a conventional diesel using the raw NIR spectral absorption and a principal component regression model. The NIR regions described included a region near 6005 cm-1 and 4425 cm-1-4430 cm-1. Knothe used only a single source of soy methyl ester in the experiment.

Currently, several commercially available instruments operating in the mid-IR region can determine biodiesel content in a conventional diesel.

SUMMARY OF THE INVENTION

The present invention provides processes and systems for the analysis and/or control of a mixture of liquid hydrocarbons and biodiesel to determine biodiesel concentration includes a) measuring the near infrared absorption in a portion of the range of 800-2500 nm; in particular 1100-2500 nm used to quantify the biodiesel content, b) taking each of the absorbances measured, or a mathematical function thereof, c) performing at least one mathematical computing or statistical treatment using the above absorbances or functions as individual independent variables, d) assigning and applying weighting constants or their equivalents to the independent variables, and, optionally e) applying the above steps using known compositions to calibrate the instrument and determine the weighting constants or equivalents, and further optionally f) outputting a signal indicative of the biodiesel concentration in the mixture, based on the absorbances or functions.

In one aspect, the present invention relates to a method which utilizes a combination of selected NIR wavelengths together with mathematical techniques and statistical techniques in which measurements of absorption are made and combines these with a partial least squares (PLS) multivariate calibration regression analysis, or other statistical technique and modeling to differentiate the concentration of biodiesels. The invention is particularly preferred for the determination of the concentration of biodiesel using a partial least squares (PLS) multivariate calibration regression analysis of the second derivative absorbance spectra versus volume percent of biodiesel.

In one aspect, the present invention relates to a process for the analysis of a mixture of liquid hydrocarbons and biodiesel to determine biodiesel concentration, comprising:

a) measuring the near infrared absorption in a portion of the range of 800-2500 nm; in particular 1100-2500 nm used to quantify the biodiesel content, b) taking each of the absorbances measured, or a mathematical function thereof, c) performing at least one statistical treatment using the above absorbances or functions as individual independent variables, d) assigning and applying weighting constants or their equivalents to said independent variables, e) applying the above steps using known compositions to calibrate the instrument and determine said weighting constants or equivalents, and f) outputting a signal indicative of the biodiesel concentration in the mixture, based on said absorbances or functions.

In another aspect, the present invention relates to a process for the control of biodiesel content in a complex mixture comprising hydrocarbons and/or substituted hydrocarbons and at least type of biodiesel material, by near infrared spectroscopy, comprising predicting said biodiesel content by:

a) measuring the near infrared absorbance of at least one wavelength in a portion of the range of 800-2500 nm; in particular 1100-2500 nm to quantify the biodiesel content b) outputting a periodic or continuous signal indicative of a derivative of said absorbance in said wavelength, or wavelengths in said one or more bands or a combination of mathematical functions comprising a derivative thereof, c) mathematically converting said signal to an output signal indicative of the biodiesel content of said mixture; and d) controlling a blending or other process which correlates with biodiesel content by apparatus responsive to said output signal.

In another aspect, the present invention relates to a process for the control of biodiesel content of a complex mixture comprising hydrocarbons and/or substituted hydrocarbons and at least one type of biodiesel material by near infrared spectroscopy, comprising predicting said biodiesel content by:

a) measuring the near infrared absorbance of at least one wavelength in a portion of the range of 800-2500 nm; in particular 1100-2500 nm to quantify the biodiesel content, b) periodically or continuously outputting a periodic or continuous signal indicative of the intensity of said absorbance in said wavelength, or wavelengths in said two or more bands or a combination of mathematical functions thereof, c) mathematically converting said signal to an output signal indicative of the biodiesel content of said mixture, d) controlling a blending or other process which correlates with biodiesel content by apparatus responsive to said output signal, wherein said mathematically converting includes taking a first or higher derivative, and wherein said output signal is used to control proportioning pumps, automatic control valves, or other flow control means to control the addition rate of each of a series of components fed from different sources to provide a target biodiesel content in a finished blended mixture.

In another aspect, the present invention relates to a process for the control of biodiesel content of a complex mixture comprising hydrocarbons and/or substituted hydrocarbons and at least one type of biodiesel content by near infrared spectroscopy, comprising predicting said biodiesel content by:

a) measuring the near infrared absorbance of at least one wavelength in a portion of the range of 800-2500 nm; in particular 1100-2500 nm to quantify the biodiesel content b) outputting a periodic or continuous signal indicative of the intensity of said absorbance in said wavelength, or wavelengths in said one or more bands or a combination of mathematical functions thereof, c) mathematically converting said signal to an output signal indicative of the biodiesel content of said mixture, d) controlling a blending or other process which correlates with biodiesel content by apparatus responsive to said output signal.

In another aspect, the present invention relates to a process for the control of hydrocarbons and substituted hydrocarbons and biodiesel material in a complex mixture to determine biodiesel content concentration, comprising, in combination:

a) measuring the near infrared absorbance of at least one wavelength in a portion of the range of 800-2500 nm; in particular 1100-2500 nm to quantify the biodiesel content b) taking each of the absorbances measured, or a mathematical function thereof, c) performing statistical treatment using said absorbances or functions as the individual independent variables, d) assigning and applying weighting constants or their equivalents to said independent variables, e) applying the above steps using known compositions in a calibration step to calibrate the instrument and determine said weighting constants or equivalents, f) repeating said steps a) and b) with unknown compositions, applying the weighting constants or equivalents determined during said calibration with known compositions to output a signal or signals indicative of a biodiesel component or biodiesel components concentration, and g) controlling blending, hydrocarbon refining or chemical process by means of apparatus responsive to said signal or signals.

In another aspect, the present invention relates to a process for the analysis and control of hydrocarbons and substituted hydrocarbons and at least one type of biodiesel material in complex mixtures to determine component concentration, the improvement comprising, in combination:

a) measuring the near infrared absorbance of at least one wavelength in a portion of the range of 800-2500 nm; in particular 1100-2500 nm to quantify the biodiesel content b) outputting a periodic or continuous signal indicative of a derivative of said absorbance in said wavelength or wavelengths in said band, or of a combination of mathematical functions thereof, c) performing statistical treatment using said signal derivative of said absorbance or functions as the individual independent variables, d) assigning and applying weighting constants or their equivalents to said independent variables, e) applying the above steps using known compositions in a calibration step to calibrate the instrument and determine said weighting constants or equivalents, f) repeating said steps a) and b) with unknown compositions, applying the weighting constants or equivalents determined during said calibration with known compositions to output a signal or signals indicative of a biodiesel component or biodiesel components concentration, and g) controlling a blending, hydrocarbon refining or chemical process by apparatus responsive to said output signal.

In certain embodiments, the following features are also present:

the mixture comprises diesel fuel and biodiesel material;

the statistical treatment comprises partial least squares analysis over the length of each band, of wavelengths, or of a portion thereof;

the mixture flows substantially intermittently or continuously past the point of measuring said absorbance;

at least one derivative of said absorbance is computed;

at least a second derivative of absorbances are measured;

the mathematical converting comprises a baseline off-set correction, and in certain embodiments, the mathematically converting or statistical treatment comprises partial least squares analyses, principle component regression, Gauss-Jordan Row reduction, multiple regression analysis, or multiple linear regression;

the signal controls a fuel blending system feeding blending components having different biodiesel compositions into a common zone, whereby a product having a desired biodiesel composition is produced;

the mixture is a stream and at least one further output signal is indicative of hydrocarbon content by measuring the near infrared absorbance of at least one wavelength, in two or more bands selected from the range of 800-2500 nm; and the composition comprises fatty acid methyl esters and or mixtures thereof; and/or middle distillate fuels which include diesel fuels, kerosenes, jet fuels and other fuel oils.

In yet another aspect, the present invention relates to a system for blending hydrocarbon and/or substituted hydrocarbon feeds and at least one type of biodiesel material, comprising, in combination:

a) measuring the near infrared absorbance of at least one wavelength in a portion of the range of 800-2500 nm; in particular 1100-2500 nm which are used to quantify the biodiesel content b) computer means for mathematically converting said signal to an output indication of biodiesel content or other measure of fuel quality; and, c) flow control means responsive to said output, for controlling respective flows of said feeds to produce a blended mixture having substantially a preset value of said biodiesel. The computer means can take a first or higher derivative of said signal. The flow control means can control the flow of streams of the hydrocarbon and/or substituted hydrocarbon feeds and streams of the at least one biodiesel material.

Other objects and advantages of the present invention will become apparent to those skilled in the art upon a review of the following detailed description of the preferred embodiments and the accompanying drawings.

BRIEF DESCRIPTION OF THE DRAWINGS

FIG. 1 is a Table 1 which shows Diesel and Biodiesel sources used to prepare additized biodiesel to evaluate NIR spectroscopy, with results reported at the 2% level.

FIG. 2 is a Table 2 which shows Diesel Matrix and Biodiesel sources used to prepare mixtures to evaluate NIR for predicting volume % biodiesel, with reported results.

FIG. 3 is a Table 3 which shows Biodiesel and Diesel Matrix used to derive the NIR calibration equation.

FIG. 4 is a Table 4 which shows NIR calculated versus volume % biodiesel added in the calibration set.

FIG. 7 is a Table 5 which shows repeatability data for 2% biodiesel from a Terminal in one sample of diesel.

DETAILED DESCRIPTION OF THE PREFERRED EMBODIMENT(S)

Signal Processing

Figure 5:
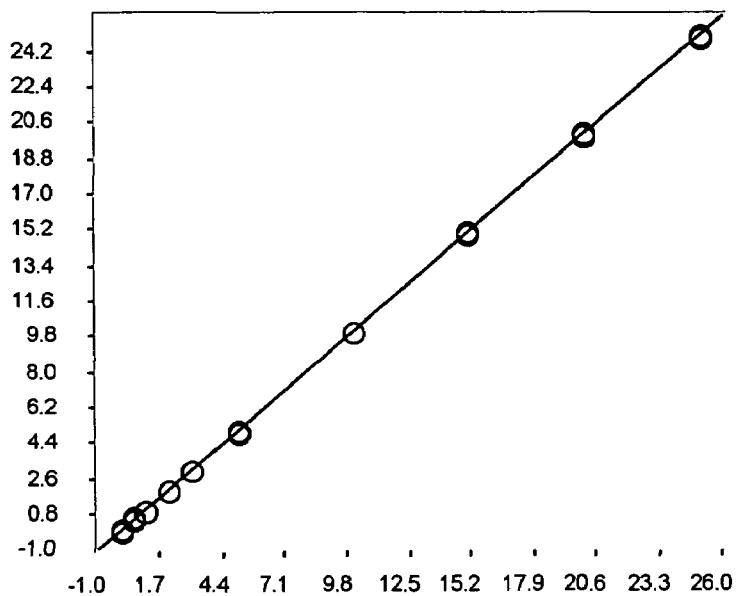
FIG. 5 is a graph which shows NIR calculated versus volume % additized biodiesel for samples in the calibration set.

As those skilled in the art will be aware, the absorbance signal from the measurement of the characteristic hydrocarbon species bands, used either solely or in conjunction with other bands, will preferably be mathematically processed to provide derived signals which are indicative of the concentrations (or property) being measured. Preferred techniques for mathematical processing are absorbance base line off-set corrected absorbance data; taking the first, second, third, fourth or higher derivative of the absorbance spectrum; the technique of dividing the absorbance at one wavelength by another; spectral subtraction; and various combinations of these mathematical techniques. Also valuable are the well-known curve fitting techniques of Savitsky-Golay and Kubelka-Munk, and N-point smoothing (signal averaging). Other types of statistical data treatment comprise principle component analysis/regression (PCA/PCR), partial least squares (PLS), Gauss-Jordan Row reduction, etc. In these techniques, correlations are found among the constituent values of interest and one or more mathematically determined equivalent weighting constants.

By equivalent weighting constant we mean to include, among other mathematical constructions known to the art, the wavelength coefficients of multiple linear regression, the factors of partial least squares regression, the scores of principal component regression, or the constants obtained from the Gauss-Jordan Row reduction algorithm. (See Harald Martens and Tormod Naes, Multivariate Calibration, John Wiley & Sons; New York, 1989) ISBN 471-90979-3!, and Honigs, D. E., Heiftje, G. M.; Hirschfeld, T., Applied Spectroscopy, 38(3), 1984, p. 317.) Also any constant obtained from any statistical calibration could be used to calculate values for unknown samples.

All biodiesels are based on triglycerides, three fatty acids bound by glycerol. If the source is animal fat, e.g., tallow or lard or whale oil, the fatty acids are saturated, that is they contain no double bonds. If the source is vegetable, the fatty acids are unsaturated, they contain one or more double bonds. Some highly unconventional sources have also been studied, including over 20 years of work on making biodiesel from algae, as reported in Biodiesel from Algae, A Look Back at the U.S. Department of Energy's Aquatic Species Program, which reported that the algae species studied in the program could produce up to 60% of their body weight in the form of triacylglycerols, the same natural oil made by oilseed crops. One preferred route to form biodiesel is to break the fatty acids free from the glycerol.

Certain preferred biodiesel material comprises a mixture of fatty acids esters. Typically these materials are made by the transesterification of vegetable oil to biodiesel. One route to biodiesel involves reacting a vegetable oil (a triglyceride) with an alcohol, preferably methanol, to form biodiesel and glycerol. The biodiesel produced from vegetable oil may have the formula: R—(C=O)—O—CH3 where R is typically 16-18 carbon atoms and may contain one or more C=C bonds. In certain embodiments, the slurry of the present invention comprises a liquid carrier comprising from about 10 to about 50% biodiesel material. More details on biodiesel manufacture may be taken from U.S. Pat. No. 6,348,074; U.S. Pat. No. 6,015,440; U.S. Pat. No. 6,203,585; U.S. Pat. No. 6,174,501 and U.S. Pat. No. 6,235,104, which are incorporated by reference.

Biodiesels are attractive for fuels, among other uses, because they have a low vapor pressure, are non-toxic and are stable, as per HMIS regulation, and do not deteriorate or detonate upon mild heating. Chemically, biodiesels are generally defined as the mono alkyl esters of long chain fatty acids derived from renewable lipid sources. Biodiesel is aliphatic, contains no sulfur, has no ring structures or aromatics, and is relatively in low molecular weight, as compared to hydrocarbon typically found in fuels. Also, biodiesel also contains large amounts of oxygen, approaching 10%. Until the present invention is was believed that a linear, relatively low molecular weight, aliphatic molecule such as biodiesel could not be detected using spectrophotometric analyses. However, it was surprisingly found by the inventors herein that the aliphatic biodiesel can be detected using the method described herein.

Utility of the Invention

This invention will find its greatest application in the petroleum refining industry and can be used to monitor the amounts of individual biodiesel species in middle distillate fuels e.g. biodiesel content in diesel fuels, kerosenes, jet fuels and other fuel oils.

Another preferred application is to feed any minimum required biodiesel content for reformulated fuel regulations into a middle distillates fuels blending system using a blending program and/or blending optimization programs.

Process conditions can be adjusted to optimize the required amounts of biodiesel to be added to the fuel.

A multiplexed or multistreamed on-line NIR can be configured so that the feed and amount of biodiesel present in the fuel can be determined by a single NIR.

An on-line NIR with closed-loop control can be used to optimize biodiesel yield in the fuel, and to minimize waste. The control system is capable of adjusting the biodiesel/fuel ratio, based on NIR measurements in the feed or product streams. From an economic standpoint, it is often not practical to maximize the biodiesel/diesel fuel ratio, but rather to operate at an optimum ratio which can be lower than the maximum attainable ratio. Consequently, control of this parameter is of utmost importance. Calculation of the biodiesel/diesel fuel ratio requires acknowledge of the percent biodiesel charge stream, and any recycle stream.

Gas chromatographs are not useful to determine these parameters. Chromatography is a slow process in comparison to an on-line spectrophotometric method such as NIR. Therefore, it is advantageous to incorporate NIR according to the invention for feed-forward control in these streams.

A multiplexed or multistreamed on-line NIR can be configured so that the feed and amount of biodiesel can be determined by a single NIR. The NIR can determine the amount of biodiesel present in the fuel, and predict the optimum biodiesel/fuel ratio.

Finally, the quality of a biodiesel/fuel blend can be verified by NIR speciation in a feedback on-line mode.

The invention will find many applications of biodiesel analysis outside of the petroleum industry. An example is the monitoring of individual biodiesel concentrations in the chemical industry. Also, the invention can be used to monitor the purity of various streams, the concentration changes which occur during a chemical reaction, and even impurity concentration of biodiesel constituents.

Analytical Equipment

Near infrared (NIR) spectrometers, Fourier Transform near infrared (FTNIR) spectrometers, and modified near infrared spectrometers of conventional design may be used with the invention. Preferred modes of operation are transmission, reflectance, and transflectance. More preferred are transmission and transflectance. Most preferred is transflectance. Suitable spectrometers are the Foss NIRSystems Models (both bench top and on-line versions); LT Industries PetroScan; and the Guided Wave Model 300 Series; and the Hamilton Sundstrand—Applied Instrument Technologies PIONIR models 1024 and 1024P. The spectrometer can be operated in a quality control lab, on a batch basis (receiving signals, e.g., by a sample feeding arrangement), or, more preferably, on a continuous basis in which the fluid to be measured flows through a cell or in which a probe immersed in the flowing fluid transmits optically through a fiber-optic cable to the spectrophotometer. The techniques for sampling, measuring, and signal processing can be conventional and are well known to those skilled in the art.

Blending Systems

Blending systems for use with the present invention to provide blends having desired species analysis can be of conventional design, usually involving the use of proportioning pumps or automatic control valves which control the addition rate for each of a series of components fed from different tanks or other sources. A computer receiving the output signal from the spectrophotometer can readily process the information to not only provide the target species analysis or percent of biodiesel present in the finished blended hydrocarbon, e.g., any middle distillate fuel, but also to provide the target blend at minimum cost, given the relative costs and analysis enhancement values of the components being fed to the blendingsystem.

The present invention permits the determination of biodiesels components which have previously been determined only by laboratory analysis. The invention permits this determination of different components to be made simultaneously and nearly continuously, providing on-line (or at-line) analysis without the need to return samples to control labs in refineries.

Examples of preferred blending systems include systems wherein said signal controls a fuel blending system feeding blending components having different biodiesel compositions into a common zone, whereby a product having a desired biodiesel composition is produced.

Three instruments were evaluated. Vendor A is a portable filter mid-IR instrument, Vendor B is a portable FT mid-IR instrument, and the FOSS NIRSystems Model 5000 is an on-line NIR operating in the second overtone (1100-2150 nm). A similar FOSS Model 5000 instrument is currently in use for predicting properties of finished gasoline and gasoline blending components. The NIR equation established herein this work is readily transferred to this instrument to determine volume % biodiesel in diesel fuel at the loading rack.

FIG. 1 shows Table 1 which lists the results obtained at the 2 volume % biodiesel level of eight samples prepared with various sources of fatty acid methyl ester (FAME) biodiesels used in the evaluation. The Vendor A and B instruments are pre-calibrated.

The average of the FOSS NIRsystems evaluation is 2.01% with a standard deviation of ±0.06 volume %. The NIR lower limit of detection is estimated at 0.3%. The accuracy at the 2.0% level is estimated at ±0.3% (15% relative) with repeatability of 0.14 volume %. The NIR is useful to determine % biodiesel. In the embodiments where ethyl esters of fatty acids are used, additional modeling can readily be done.

Diesel samples from seven different refineries were used in the NIR calibration set. Six were winter products and one was a summer product. Three diesel samples from one refinery collected at different times were used in the validation set. Two were winter products and one was a summer product.

The Near-IR data shows improvements in accuracy and standard deviation when compared to the results obtained on the two instruments (FIG. 1).

FIG. 2 shows Table 2 which lists the results of all samples used to validate the NIR instruments in this evaluation. The standard error of prediction (SEP) for the data are: 0.10, 0.27, and 0.58 volume % for NIRsystems, Vendor A, and Vendor B, respectively.

In the Near Infrared, the absorbances due to biodiesel are more problematic due to matrix interferences from component composition variances. This is compensated for by adding known amounts of biodiesel fuel to a wide variety of commercially-made diesels. Software that captures spectral outliers is also useful. In this evaluation, biodiesel ranging from 0 to 25 volume % was added to diesels from seven refineries to obtain a multivariate calibration equation. (Stated on preceding page-BKW).

NIR has also been used to monitor the transesterification and assessing the Biodiesel Fuel Quality (Rapid Monitoring of Transesterification and Assessing Biodiesel Fuel Quality by Near-infrared Spectroscopy Using Fiber-Optic Probe, Gerhard Knothe, Presented in part at the AOCS Annual Meeting & Expo, Chicago, Ill., May 1998) and using NIR monitoring of transesterification reaction with correlation to 1H Magnetic Resonance Spectroscopy (NMR)(Monitoring a Progressing Transesterification Reaction by Fiber-Optic Color Near Infrared Spectroscopy with Correlation to 1H Nuclear Magnetic Resonance Spectroscopy, Gerhard Knothe, Presented in part at the AOCS Annual Meeting & Expo, Chicago, Ill., May 1998). Both publications use fiber optic probes for NIR data acquisition.

Thus, an NIR on-line instrument with fiber optic probe installed in a refinery laboratory or directly monitoring a blending operation in real time is useful to monitor relative levels of biodiesel added to diesel fuels, as well as to assess the quality of biodiesel fuels. In particular, the NIR is capable of measuring accurately in the mille-absorbance units.

Preparation of Biodiesel Samples for Evaluation and Validation Purposes

Three low sulfur diesels (<0.05 wt. %) and five sources of biodiesel were used to prepare the additized diesel samples in the preliminary NIR investigation. The various sources of biodiesel fuels were taken to be 100% and equivalent to FAME content. The two vendors in this evaluation, Vendor A and Vendor B also took their sources to be 100% in deriving calibration equations.

The diesel fuel samples were produced at Refinery C and designated as:
(1) Pipeline A
(2) a Refinery C sample
(3) Refinery C Tank The biodiesel, FAME, samples used were:
(1) a sample from a Terminal A
(2) ASTM cetane round robin, biodiesel D-903 BIO
(3) soy derived, from a vendor G
(4) yellow grease derived, from a vendor G
(5) animal derived, from a vendor G Vendor A is a fixed wavelength portable instrument operating in the Mid-IR region. Two absorption bands are used to quantify the biodiesel content, the C—O stretches at 1745 and 1160 $cm^{-1}$. The instrument is also capable of determining multiple properties.

Vendor B is a mid-FTIR portable instrument.

Development of the NIR Multivariate Calibration Equation

The above five sources of biodiesel were used to prep mixtures for deriving an NIR multivariate calibration equation. FIG. 3 shows Table 3 which lists the volume % and biodiesel used in the calibration set. The initial diesel sample from each refinery was included as a 0.0% biodiesel. A total of 68 samples were used in the calibration set.

NIR spectral acquisition was obtained using a FOSS NIR-Systems' on-line Model 5000, equipped with a fiber optic bundle containing 420 fibers, and an immersion probe tip operating in the transmission mode. A path length of 8-mm (16-mm through reflectance) was used.

The spectra used in the calibration are an average of 32 scans. Second derivatives of absorption data, having a segment size of 14 nm, were used to correct for light diffraction due to haze and other effects that contribute to baseline offsets.

A Partial Least Squares (PLS) multivariate algorithm was used to derive an equation in the wavelength regions between 1140-1650 nm and 1810-2100 nm (the region between 1650-1810 is mostly saturated at this path length and therefore not used). This produced an equation of 11 factors having a standard error of calibration (SEC) of 0.07 volume %. The correlation ratio squared $R^2$ was 0.9999. The standard error of cross validation SECV was found to be 0.08 volume %. FIG. 4 shows Table 4 which lists the NIR calculated versus volume % biodiesel added in the calibration set. The data presented in FIG. 4, Table 4, is displayed graphically in FIG. 5.

Figure 6:
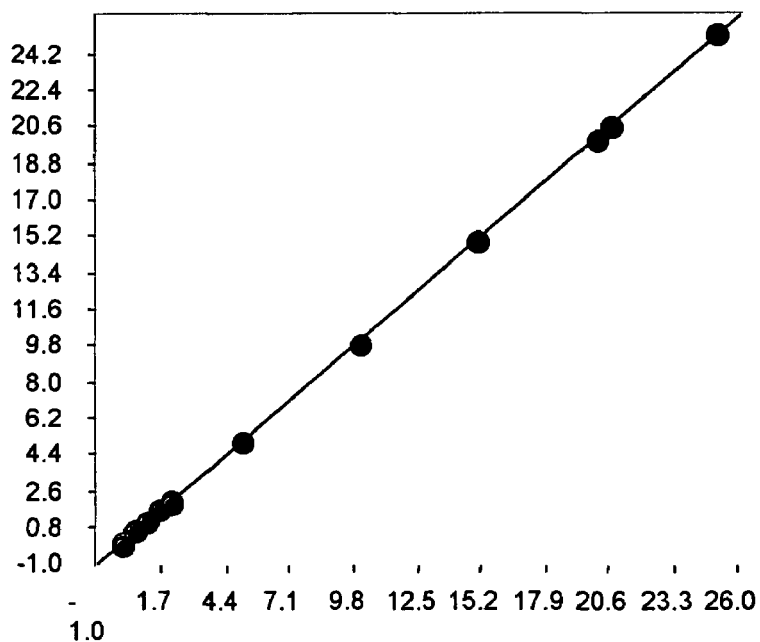
FIG. 6 is a graph which shows Validation set demonstrating the performance of the NIR equation.

The samples listed in FIG. 2, Table 2, served as an external validation set (samples not included in the calibration set) to further assess the predictive merit of the calibration equation. This data is presented graphically in FIG. 6. The standard error of prediction was calculated at 0.10 volume %. The 95% confidence limit is estimated at 0.3 volume %.

One of the 2% biodiesel in the calibration set, 2% biodiesel in Detroit diesel, was run five times to determine the repeatability of the NIR method. The repeatability of five back-to-back spectra are listed in FIG. 7 which shows in the data obtained after withdrawing (Table 5A), and cleaning the probe five times between scans (Table 5B). The repeatability at the 2.00 volume % level is estimated at 0.14 volume %.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein. For example, FTNIR or even Raman IR can be used in place of NIR by conventionally modifying the mathematical conversions and data analysis, so that spectral data obtained by FTNIR or Raman IR are used in place of the near infrared spectral data, and calibrating using one or more mathematical methods as explained above, against the biodiesel analysis or other primary method as with an NIR instrument.

We claim:

1. A process for the control of biodiesel content in a complex mixture comprising hydrocarbons and/or substituted hydrocarbons and at least one type of biodiesel material, by near infrared spectroscopy, comprising predicting said biodiesel content by:
    a) measuring the near infrared absorbance of at least one wavelength in a portion of the range of 800-2500 nm; which are used to quantify the biodiesel content,
    b) outputting a periodic or continuous signal indicative of a derivative of said absorbance in said wavelength, or wavelengths in said one or more bands or a combination of mathematical functions comprising a derivative thereof,
    c) mathematically converting said signal to an output signal indicative of the biodiesel content of said mixture; and
    d) controlling a blending or other process which correlates with biodiesel content by apparatus responsive to said output signal;
    wherein said mathematically converting includes taking a first or higher derivative, and
    wherein said output signal is used to control proportioning pumps, automatic control valves, or other flow control means to control the addition rate of each of a series of components fed from different sources to provide a target biodiesel content in a finished blended mixture.

2. A process according to claim 1 wherein said mixture comprises diesel fuel and biodiesel material.

3. A process according to claim 1 wherein said statistical treatment comprises partial least squares analysis over the length of each band, of wavelengths, or of a portion thereof.

4. A process according to claim 1, wherein said mixture flows substantially intermittently or continuously past the point of measuring said absorbance.

5. A process according to claim 1 wherein a derivative of said absorbance is computed.

6. A process according to claim 1 wherein a second derivative of absorbances are measured.

7. A process according to claim 1 wherein said mathematical converting comprises a baseline off-set correction.

8. A process according to claim 1 wherein said mathematically converting or statistical treatment comprises partial least squares analyses, principle component regression, Gauss-Jordan Row reduction, multiple regression analysis, or multiple linear regression.

9. A process according to claim 1 wherein said signal controls a fuel blending system feeding blending components having different biodiesel compositions into a common zone, whereby a product having a desired biodiesel composition is produced.

10. A process according to claim 1 wherein the mixture is a stream and at least one further output signal is indicative of hydrocarbon content by measuring the near infrared absorbance of at least one wavelength, in two or more bands selected from the range of 800-2500 nm.

11. A process according to claim 1 wherein said composition comprises fatty acid methyl esters and or mixtures thereof.

12. A process according to claim 1 wherein said hydrocarbons comprise middle distillate fuels which include diesel fuels, kerosenes, jet fuels and other fuel oils.

13. A process according to claim 1 wherein the wavelengths is in the range of 1100 to 2500 nm.

14. A process for the control of hydrocarbons and substituted hydrocarbons and biodiesel material in a complex mixture to determine biodiesel content concentration, comprising, in combination:
  a) measuring the near infrared absorbance of at least one wavelength in a portion of the range of 800-2500 nm; which are used to quantify the biodiesel content,
  b) taking each of the absorbances measured, or a mathematical function thereof,
  c) performing statistical treatment using said absorbances or functions as the individual independent variables,
  d) assigning and applying weighting constants or their equivalents to said independent variables,
  e) applying the above steps using known compositions in a calibration step to calibrate the instrument and determine said weighting constants or equivalents,
  f) repeating said steps a) and b) with unknown compositions, applying the weighting constants or equivalents determined during said calibration with known compositions to output a signal or signals indicative of a biodiesel component or biodiesel components concentration, and
  g) controlling blending, hydrocarbon refining or chemical process by means of apparatus responsive to said signal or signals;
  wherein said mathematically converting includes taking a first or higher derivative, and
  wherein said output signal is used to control proportioning pumps, automatic control valves, or other flow control means to control the addition rate of each of a series of components fed from different sources to provide a target biodiesel content in a finished blended mixture.

15. A process for the analysis and control of hydrocarbons and substituted hydrocarbons and at least one type of biodiesel material in complex mixtures to determine component concentration, the improvement comprising, in combination:
  a) measuring the near infrared absorbance of at least one wavelength in a portion of the range of 800-2500 nm; which are used to quantify the biodiesel content,
  b) outputting a periodic or continuous signal indicative of a derivative of said absorbance in said wavelength or wavelengths in said band, or of a combination of mathematical functions thereof,
  c) performing statistical treatment using said signal derivative of said absorbance or functions as the individual independent variables,
  d) assigning and applying weighting constants or their equivalents to said independent variables,
  e) applying the above steps using known compositions in a calibration step to calibrate the instrument and determine said weighting constants or equivalents,
  f) repeating said steps a) and b) with unknown compositions, applying the weighting constants or equivalents determined during said calibration with known compositions to output a signal or signals indicative of a biodiesel component or biodiesel components concentration, and
  g) controlling a blending, hydrocarbon refining or chemical process by apparatus responsive to said output signal;
  wherein said mathematically converting includes taking a first or higher derivative, and
  wherein said output signal is used to control proportioning pumps, automatic control valves, or other flow control means to control the addition rate of each of a series of components fed from different sources to provide a target biodiesel content in a finished blended mixture.

16. A system for blending hydrocarbon and/or substituted hydrocarbon feeds and at least one type of biodiesel material, comprising, in combination:
  a) NIR absorbance sensing means for emitting a signal indicative of absorbance in at least one band from a portion of the range of 800-2500 nm; selected from bands which are used to quantify biodiesel content
  b) computer means for mathematically converting said signal to an output indication of biodiesel content or other measure of fuel quality; and,
  c) flow control means responsive to said output, for controlling respective flows of said feeds to produce a blended mixture having substantially a preset value of said biodiesel.

17. A system according to claim 16, wherein said computer means take a first or higher derivative of said signal.

18. A system according to claim 16 wherein said mathematical converting comprises partial least squares analysis over the length of each band, of wavelengths, or of a portion thereof.

19. A system according to claim 16, wherein a derivative of said absorbance is computed.

20. A system according to claim 16, wherein a second derivative of absorbances are measured.

21. A system according to claim 16 wherein said mathematical converting comprises a baseline off-set correction.

22. A system according to claim 16, wherein said mathematically converting or statistical treatment comprises partial least squares analyses, principle component regression, Gauss-Jordan Row reduction, multiple regression analysis, or multiple linear regression.

23. A system according to claim 16 wherein said signal controls a fuel blending system feeding blending components having different biodiesel compositions into a common zone, whereby a product having a desired biodiesel composition is produced.

* * * * *